(12) United States Patent
Simon et al.

(10) Patent No.: US 10,018,540 B2
(45) Date of Patent: Jul. 10, 2018

(54) CLEARING AGENT AND MOUNTING MEDIA FOR MICROSCOPY

(71) Applicant: Rutgers, The State University of New Jersey, New Brunswick, NJ (US)

(72) Inventors: James E. Simon, Princeton, NJ (US); Thomas Villani, New Brunswick, NJ (US); Adolfina Koroch, Highland Park, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 23 days.

(21) Appl. No.: 15/277,118

(22) Filed: Sep. 27, 2016

(65) Prior Publication Data

US 2017/0016808 A1    Jan. 19, 2017

Related U.S. Application Data

(63) Continuation-in-part of application No. 15/258,474, filed on Sep. 7, 2016, which is a continuation-in-part of application No. 14/391,106, filed on Oct. 7, 2014, now Pat. No. 9,464,971, said application No. 15/258,474 is a continuation of application No. 14/391,106, filed as application No. PCT/US2013/035761 on Apr. 9, 2013, now Pat. No. 9,464,971.

(60) Provisional application No. 61/622,210, filed on Apr. 10, 2012.

(51) Int. Cl.
*G01N 1/30* (2006.01)

(52) U.S. Cl.
CPC ......... *G01N 1/30* (2013.01); *G01N 2001/307* (2013.01)

(58) Field of Classification Search
CPC ................... G01N 2001/307; G01N 2001/302
See application file for complete search history.

(56) References Cited

U.S. PATENT DOCUMENTS

| 3,961,097 | A | 6/1976 | Gravlee, Jr. |
| 4,120,991 | A | 10/1978 | Ornstein et al. |
| 6,451,260 | B1 | 9/2002 | Dusterhoft et al. |
| 7,569,130 | B2 | 8/2009 | Edwards et al. |
| 2007/0134798 | A1 | 6/2007 | McCormick et al. |
| 2010/0124750 | A1 | 5/2010 | Stocker et al. |

FOREIGN PATENT DOCUMENTS

| CA | 2198520 A1 | 4/1998 |
| WO | 1994/004906 | 3/1994 |
| WO | 2009/086487 | 7/2009 |
| WO | 2010/065400 | 6/2010 |

OTHER PUBLICATIONS

Baumgartner et al., "Plant histology as an aid in squirrel food-habit studies," J Wildlife Management 3(3)266-268, 1939.

(Continued)

*Primary Examiner* — Rosanne Kosson
(74) *Attorney, Agent, or Firm* — Fox Rothschild LLP

(57) ABSTRACT

A clearing agent and mounting solution for microscopy is disclosed comprising at least trichloroethanol and/or derivatives thereof, where the refractive index of the solution is greater than or equal to about 1.3810. Also disclosed are methods of preparing specimens for microscopy.

15 Claims, 14 Drawing Sheets

(56) References Cited

OTHER PUBLICATIONS

International Preliminary Report on Patentability for PCT/US2013/035761, dated Oct. 14, 2014.
International Search Report for PCT/US2013/035761, dated Jul. 23, 2013.
Moreira et al., "Kinematic viscosity and refractive index of aqueous solutions of ethanol and glycerol," Ind Eng Chem Res 48:2157-2161, 2009.
Supplementary European Search Report for European Patent Application No. 137752663, dated Oct. 14, 2015.
Written Opinion of the International Search Authority for PCT/US2013/035761, dated Jul. 23, 2013.
U.S. Appl. No. 14/391,106, filed Oct. 7, 2014, Clearing agent and mounting medium for microscopy.
U.S. Appl. No. 15/258,474, filed Sep. 7, 2016, Clearing agent and mounting medium for microscopy.

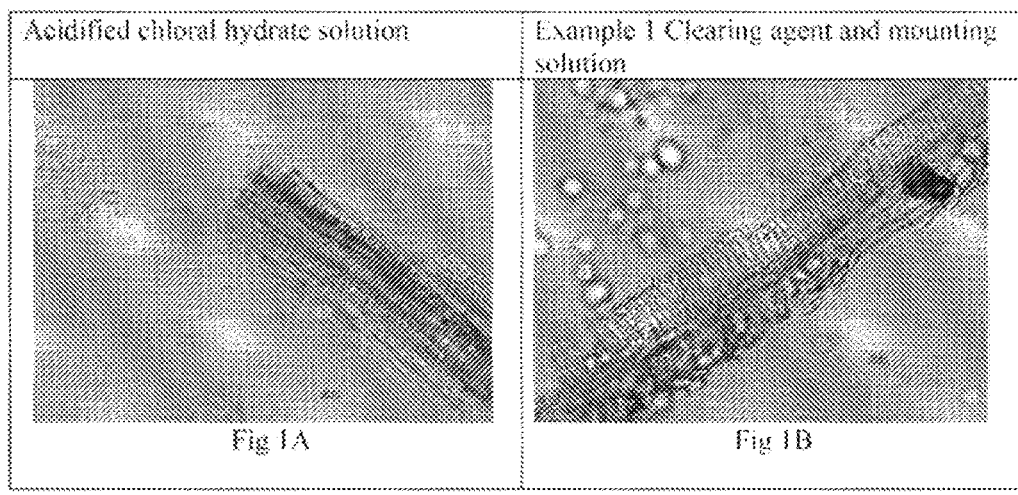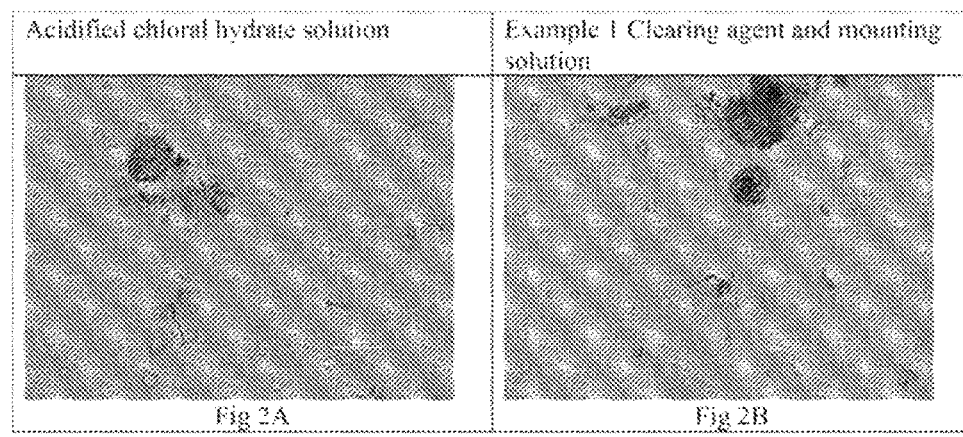

| Acidified chloral hydrate solution | Example 1 Clearing agent and mounting solution |
|---|---|
| 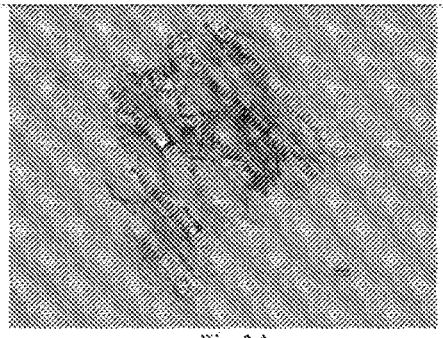 | 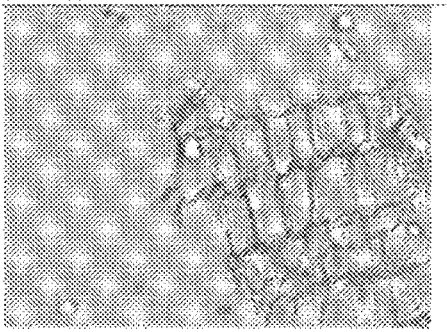 |
| Fig 3A | Fig 3B |
| Acidified chloral hydrate solution | Example 1 Clearing agent and mounting solution |
|---|---|
| 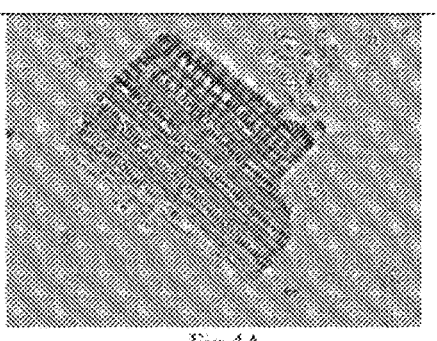 | 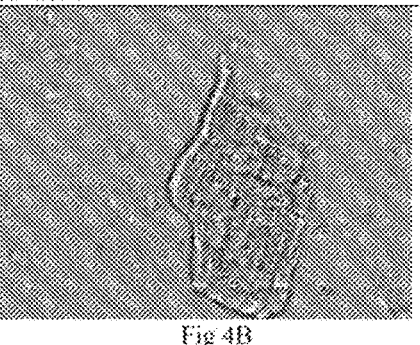 |
| Fig 4A | Fig 4B |

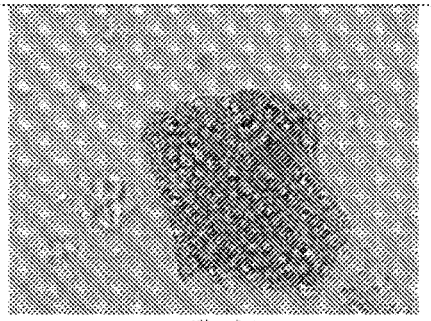
Fig 5A — Acidified chloral hydrate solution
Fig 5B — Example 1 Clearing agent and mounting solution
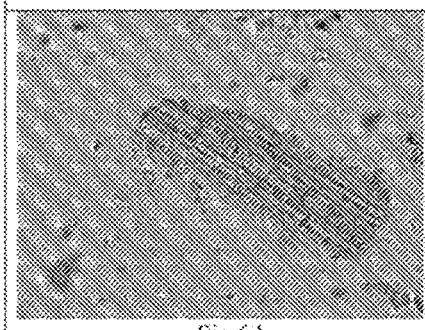
Fig 6A — Acidified chloral hydrate solution
Fig 6B — Example 1 Clearing agent and mounting solution

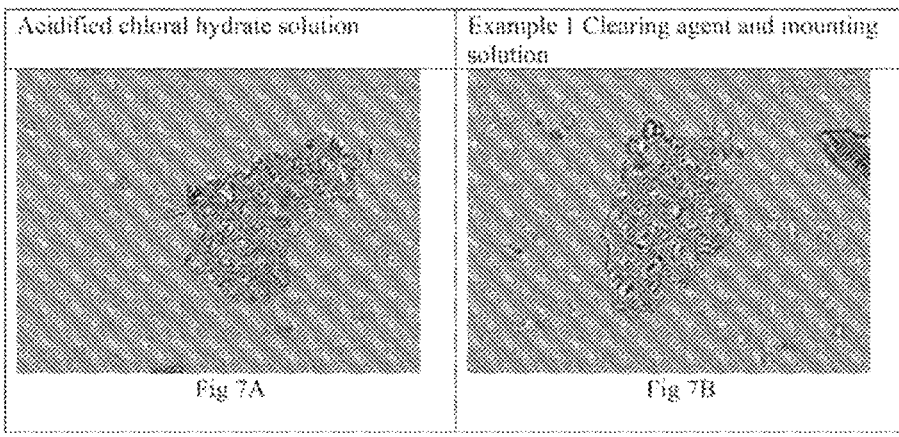
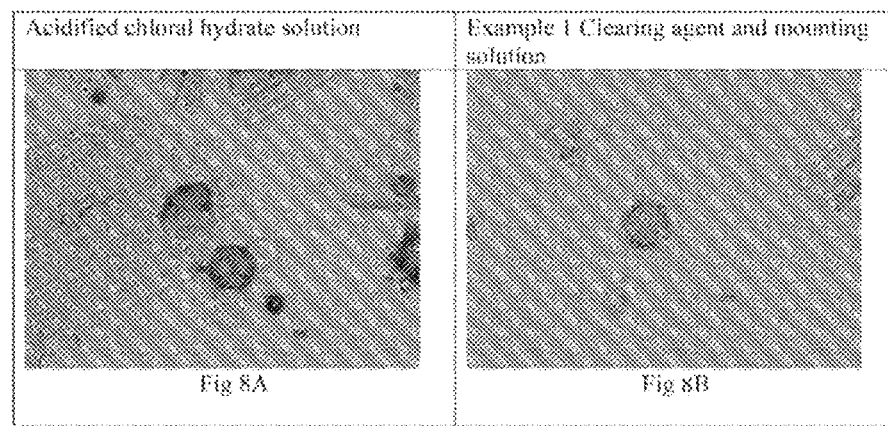

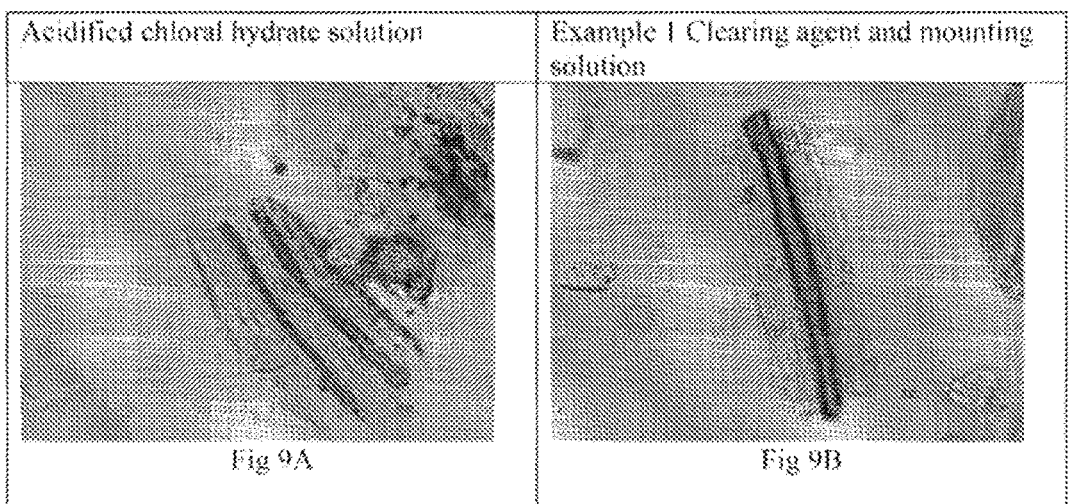

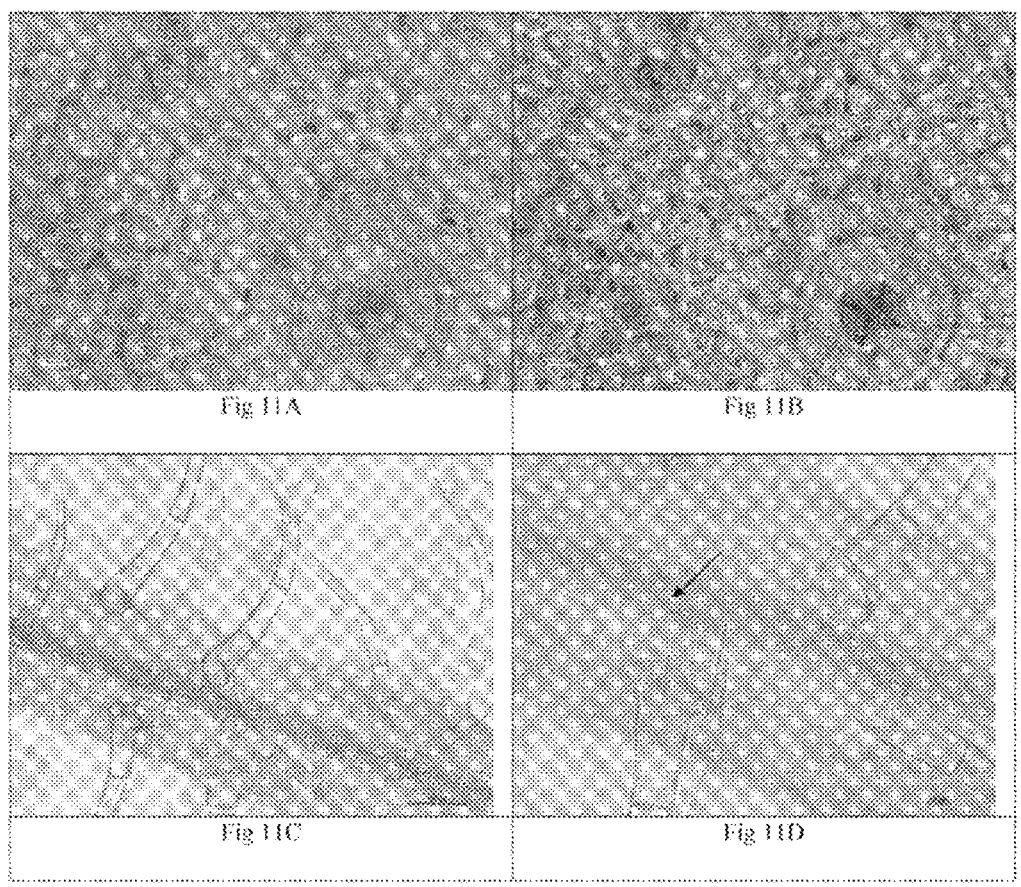

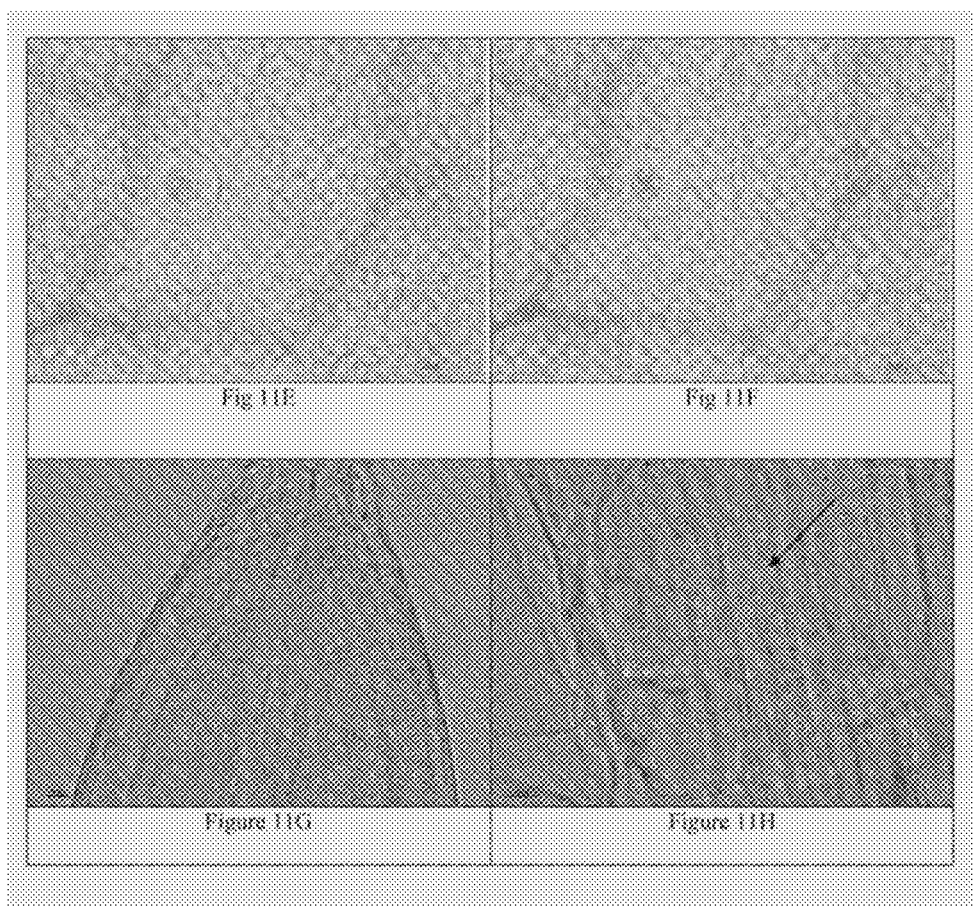

A               B               C

CLEARING AGENT AND MOUNTING MEDIA FOR MICROSCOPY

CROSS-REFERENCE TO RELATED APPLICATIONS

This application is a Continuation-in-Part of U.S. application Ser. No. 15/258,474, filed on Sep. 7, 2016, and also a Continuation-in-Part of U.S. application Ser. No. 14/391,106, filed on Oct. 7, 2014; U.S. application Ser. No. 15/258,474 is a continuation of U.S. application Ser. No. 14/391,106, filed on Oct. 7, 2014, which is a 371 National Phase of PCT/US2013/035761 filed Apr. 9, 2013, which claims the benefit of priority to U.S. Application No. 61/622,210 filed Apr. 10, 2012, the entire disclosures of which are incorporated herein by reference.

FIELD OF THE INVENTION

The present application is related to microscopy, and more particularly, to a clearing agent and mounting media for microscopy.

BACKGROUND

There are different methods for identification of materials, including macroscopic, chemical and microscopic identification, among others. Microscopic identification is a technique that uses a microscope to identify characteristic features of living organisms, parts of an organism, cells or sub-cellular organs, as well as minerals or other non-living materials. The importance of microscopy resides in the ability to clearly identify differences between organisms or their parts by focusing on specific characteristics or diagnostic structures. Microscopy relies on dependable, readily available reagents as clearing agent and mounting solutions, optionally used in conjunction with stains in order to visualize the materials under the slide.

The general microscopy procedure for specimens derived from living organisms comprises mounting a small sample of the tissue to be analyzed in a solvent solution and observing it under the microscope. In many cases the cell contents obscure the tissues, making it difficult to identify characteristic features. Differences in refractive index within the specimen prohibit visualization of deeper visual planes, and occlude detail from observation. In these cases a clearing solution is applied in order to improve the transparency of the specimen, allowing one to visualize multiple vertical layers of the specimen without careful sectioning or remounting. This increased transparency and improved clarity allows the microscope user to visualize across a full range of vertical planes in the sample, allowing the user to select interesting focal planes by adjusting the focus.

An almost universally used clearing agent for microscopy is acidified chloral hydrate glycerol solution (chloral hydrate solution acidified with hydrochloric acid), also known as Hertwig's solution. Acidified chloral hydrate solution is used in botanical microscopy, mycology, entomology, histology, mineralogy, food science, quality control, forensics, nematology, archeology, paleontology, virology, immunology, microscopy including, but not limited to, differential interference contrast microscopy, electron microscopy, fluorescence microscopy, confocal microscopy, and other related applications of microscopy and optics. Chloral hydrate, when applied to botanical samples, dissolves cellular contents and intercellular substances thus allowing cell walls and shapes of the cells to be easily observed. Consequently, chloral hydrate has become the industry standard for many laboratories focused on quality assessment of herbal products.

Unfortunately, chloral hydrate, the key component in acidified chloral hydrate solution, is considered under US law to be a narcotic hypnotic, and as such is a DEA (Drug Enforcement Administration) scheduled substance, requiring DEA approval and compliance in order to purchase and/or possess it. This has precluded scientists from being able to purchase this reagent. Furthermore, maintaining DEA compliance is a costly, tedious, and time-consuming process.

Therefore, cost-effective, readily available, and unregulated replacements for acidified chloral hydrate solution are needed as clearing and mounting agents for microscopy.

SUMMARY

It has now been discovered that aqueous solutions of trichloroethanol, or its derivatives or analogs, with or without other additives, can effectively replace acidified chloral hydrate solution as a clearing and mounting medium for microscopy.

This discovery has been exploited to develop the present disclosure, which, in one aspect, is the clearing agent and mounting solution comprising 10% to 97% (v/v) trichloroethanol or derivative thereof. In some embodiments, the mounting solution and clearing agent further comprises 16.5% to 36% (v/v) benzyl alcohol, 12.5% to 50% glycerol, polyethylene glycol (PEG), propylene glycol (PG), ethylene glycol (EG), and/or derivatives thereof, and optionally water.

In yet another aspect, a clearing agent and mounting solution comprising 5% to 97% (v/v) trichloroethanol or derivative thereof 16.5% to 36% (v/v) benzyl alcohol; 12.5% to 50% glycerol, polyethylene glycol (PEG), propylene glycol (PG), ethylene glycol (EG), and/or derivatives thereof and optionally water.

In some embodiments, the clearing agent and mounting solution comprises 36% (v/v) of trichloroethanol or derivative thereof; 36% (v/v) benzyl alcohol; and 27% (v/v) glycerol. In other embodiments, the clearing agent and mounting solution comprises 33% (v/v) of trichloroethanol or derivative thereof; 33% (v/v) benzyl alcohol; and 33% (v/v) glycerol. In yet other embodiments, the clearing agent and mounting solution comprises 33% (v/v) trichloroethanol or derivative thereof; 33% (v/v) benzyl alcohol; 17% (v/v) glycerol; and 17% (v/v) benzyl benzoate. In still other embodiments, the clearing agent and mounting solution comprises 29% (v/v) trichloroethanol or derivative thereof 29% (v/v) benzyl alcohol; 17% (v/v) glycerol; 13% (v/v) benzyl benzoate; and 13% (v/v) benzyl ether.

In certain embodiments, a clearing agent and mounting solution comprises 42% (v/v) trichloroethanol or derivative thereof; 16.5% (v/v) benzyl alcohol; 16.5% (v/v) glycerol; and 25% (v/v) benzyl ether. In other embodiments, the clearing agent and mounting solution comprises 36% (v/v) of trichloroethanol or derivative thereof; 36% (v/v) benzyl alcohol; and 27% (v/v) PEG, PG, EG, and/or derivatives thereof. In yet another embodiment, the clearing agent and mounting solution comprises 33% (v/v) of trichloroethanol or derivative thereof; 33% (v/v) benzyl alcohol; and 33% (v/v) PEG, PG, EG, and/or derivatives thereof. In still other embodiments, the clearing agent and mounting solution comprises 33% (v/v) of trichloroethanol or derivative thereof; 33% (v/v) benzyl alcohol; 17% (v/v) PEG, PG, EG. and/or derivatives thereof; and 17% (v/v) benzyl benzoate.

In some embodiments, the clearing agent and mounting solution comprise 29% (v/v) of trichloroethanol or derivative thereof; 29% (v/v) benzyl alcohol; 17% (v/v) PEG, PG, EG. and/or derivatives thereof 13% (v/v) benzyl benzoate; and 13% (v/v) benzyl ether. In certain embodiments, the clearing agent and mounting solution comprises 42% (v/v) trichloroethanol or derivative thereof; 16.5% (v/v) benzyl alcohol; 16.5% (v/v) PEG, PG, EG. and/or derivatives thereof and 25% (v/v) benzyl ether. In other embodiments, the trichloroethanol derivative comprises mono- or poly-halogenated branched or unbranched alcohols, diols, glycols, aldehydes, aldehyde-hydrates, hemi-acetals, acetals, ketals, aminals, and hemi-aminals of at least 2 carbon units, where branches are defined as any mono- or poly-halogenated aliphatic or aromatic side chains containing hydroxyl, amino, ether, carboxyl, carboxyamido, carbonate, carbamyl, carbonyl-chloride, polyethylene glycol, or aminoethanol groups, and a polymer thereof. In other embodiments, the clearing agent and mounting solution further comprises C1-C6 alcohol. In yet other embodiments, the clearing agent and mounting solution further comprises a solidification aid comprising polyethylene glycol, polyamide resin, polyvinylpyrrolidone, polyvinyl alcohol, or mixtures thereof.

In another aspect, the disclosure provides a clearing agent and mounting solution comprising 5% to 90% (v/v) trichloroethanol or derivative thereof; and 5% to 90% (v/v) benzyl alcohol. In some embodiments, the clearing agent and mounting solution comprises 10% to 90% (v/v) trichloroethanol or derivative thereof and 10% to 90% (v/v) benzyl alcohol. In other embodiments, the clearing agent and mounting solution further comprises PEG. EG, PG, and/or derivatives thereof. In yet other embodiments, the clearing agent and mounting solution further comprises C1-C6 alcohol. In still other embodiments, the clearing agent and mounting solution further comprises a solidification aid comprising polyethylene glycol, polyamide resin, polyvinylpyrrolidone, polyvinylalcohol, or mixtures thereof. In certain embodiments, the trichloroethanol derivative comprises mono- or poly-halogenated branched or unbranched alcohols, diols, glycols, aldehydes, aldehyde-hydrates, hemi-acetals, acetals, ketals, aminals, and hemi-aminals of at least 2 carbon units, wherein branches are a mono- or poly-halogenated aliphatic or aromatic side chains comprising hydroxyl, amino, ether, carboxyl, carboxyamido, carbonate, carbamyl, carbonyl-chloride, polyethylene glycol, or aminoethanol groups, and polymers thereof.

In yet another aspect, the disclosure provides a clearing agent and mounting solution comprising 5% to 90% (v/v) trichloroethanol or derivative thereof; and 5% to 90% (v/v) benzyl benzoate. In some embodiments, the clearing agent and mounting solution comprises 10% to 90% (v/v) trichloroethanol or derivative thereof; and 10% to 90% (v/v) benzyl benzoate. In other embodiments, the clearing agent and mounting solution further comprises PEG. EG, PG, and/or derivatives thereof. In yet other embodiments, the clearing agent and mounting solution further comprises C1-C6 alcohol. In still other embodiments, the clearing agent and mounting solution further comprises a solidification aid comprising polyethylene glycol, polyamide resin, polyvinylpyrrolidone, polyvinylalcohol, or mixtures thereof. In certain embodiments, the trichloroethanol derivative comprises mono- or poly-halogenated branched or unbranched alcohols, diols, glycols, aldehydes, aldehyde-hydrates, hemi-acetals, acetals, ketals, aminals, and hemi-aminals of at least 2 carbon units, wherein branches are a mono- or poly-halogenated aliphatic or aromatic side chains comprising hydroxyl, amino, ether, carboxyl, carboxyamido, carbonate, carbamyl, carbonyl-chloride, polyethylene glycol, or aminoethanol groups, and polymers thereof.

In still another aspect, the disclosure provides a clearing agent and mounting solution comprising 5% to 90% (v/v) trichloroethanol or derivative thereof; 5% to 90% (v/v) benzyl alcohol; and 5% to 90% (v/v) benzyl benzoate. In some embodiments, the clearing agent and mounting solution comprises 10% to 90% (v/v) trichloroethanol or derivative thereof; 10% to 90% (v/v) benzyl alcohol; and 10% to 90% (v/v) benzyl benzoate. In other embodiments, the clearing agent and mounting solution comprises 25% to 50% (v/v) trichloroethanol or derivative thereof; 25% to 50% (v/v) benzyl alcohol; and 33% (v/v) benzyl benzoate. In yet other embodiments, the clearing agent and mounting solution comprises 33% (v/v) of trichloroethanol or derivative thereof; 33% (v/v) benzyl alcohol; and 33% (v/v) benzyl benzoate. In still other embodiments, the clearing agent and mounting solution further comprises PEG. EG, PG, and/or derivatives thereof. In certain embodiments, the clearing agent and mounting solution further comprises C1-C6 alcohol. In some embodiments, the clearing agent and mounting solution further comprises a solidification aid comprising polyethylene glycol, polyamide resin, polyvinylpyrrolidone, polyvinylalcohol, or mixtures thereof. In other embodiments, the trichloroethanol derivative comprises mono- or poly-halogenated branched or unbranched alcohols, diols, glycols, aldehydes, aldehyde-hydrates, hemi-acetals, acetals, ketals, aminals, and hemi-aminals of at least 2 carbon units, wherein branches are a mono- or poly-halogenated aliphatic or aromatic side chains comprising hydroxyl, amino, ether, carboxyl, carboxyamido, carbonate, carbamyl, carbonyl-chloride, polyethylene glycol, or aminoethanol groups, and polymers thereof.

In another aspect, the disclosure provides a clearing agent and mounting solution comprising 5% to 90% (v/v) of trichloroethanol or derivative thereof; and 5% to 90% (v/v) benzyl ether. In some embodiments, the clearing agent and mounting solution comprises 25% (v/v) of trichloroethanol or derivative thereof and 25% (v/v) benzyl ether. In other embodiments, the clearing agent and mounting solution comprises 50% (v/v) of trichloroethanol or derivative thereof; and 50% (v/v) benzyl ether. In yet other embodiments, the clearing agent and mounting solution further comprises 25% (v/v) benzyl alcohol; and 25% (v/v) benzyl benzoate. In still other embodiments, the clearing agent and mounting solution comprises 33% (v/v) of trichloroethanol or derivative thereof 33% (v/v) benzyl ether; and 33% (v/v) benzyl alcohol. In certain embodiments, the clearing agent and mounting solution further comprises PEG. EG, PG, and/or derivatives thereof. In other embodiments, the clearing agent and mounting solution further comprises C1-C6 alcohol. In yet other embodiments, the clearing agent and mounting solution further comprises a solidification aid comprising polyethylene glycol, polyamide resin, polyvinylpyrrolidone, polyvinylalcohol, or mixtures thereof. In still other embodiments, the trichloroethanol derivative comprises mono- or poly-halogenated branched or unbranched alcohols, diols, glycols, aldehydes, aldehyde-hydrates, hemi-acetals, acetals, ketals, aminals, and hemi-aminals of at least 2 carbon units, wherein branches are a mono- or poly-halogenated aliphatic or aromatic side chains comprising hydroxyl, amino, ether, carboxyl, carboxyamido, carbonate, carbamyl, carbonyl-chloride, polyethylene glycol, or aminoethanol groups, and polymers thereof.

In another aspect, the disclosure provides a method of preparing a specimen for microscopy, comprising soaking a specimen in sufficient quantity of a clearing solution according to the disclosure for at least about 1 minute to about 12 months to provide a cleared specimen; applying the cleared specimen to a microscope slide, cuvette, or well for observation; and optionally, applying a cover slip.

In yet another aspect, after soaking the specimen, the cleared specimen is applied to a resin which solidifies, and then is cast into a solid for examination or indefinite storage.

In another aspect, after soaking the specimen, a solution of 5%-20% polyvinylpyrrolidone in methanol is applied to the cleared specimen, which optionally is dried at 50° C.-90° C. until hardened.

In yet another aspect, after soaking the specimen, a stain or dye is applied to the cleared specimen to provide a cleared stained specimen, whereby the features of the specimen are selectively highlighted. The cleared stained specimen is applied to a microscope slide, cuvette, or well for observation, and optionally, is covered with a cover slip. The stain or dye can be a fluorescent stain or dye, so that the cleared stained specimen can be visualized using a fluorescent and/or epifluorescent and/or confocal microscope.

Another aspect is directed to a method of preparing a specimen for spectrophotometric analysis, comprising applying a specimen to a cuvette; and applying a sufficient quantity of a clearing agent and mounting solution according to the disclosure to mount said specimen.

In another aspect, the disclosure provides a method of preparing a specimen for microscopy, comprising soaking a specimen in sufficient quantity of a clearing agent and mounting solution according to the disclosure for at least about 1 minute to about 12 months to provide a cleared specimen; applying the cleared specimen to a microscope slide, cuvette, or well for observation; and optionally, applying a cover slip.

Alternatively, in another aspect, after soaking the specimen in a clearing agent according to the disclosure, the cleared specimen is applied to a resin which solidifies, and then is cast into a solid for examination or indefinite storage.

In yet another aspect, after soaking the specimen in a clearing agent according to the disclosure, a solution of 5%-20% polyvinylpyrrolidone in methanol is applied to the cleared specimen, which optionally is dried at 50° C.-90° C. until hardened.

In still another aspect, after soaking the specimen in a clearing agent and mounting solution according to the disclosure, a stain or dye is applied to the cleared specimen to provide a cleared, stained specimen, whereby the features of the specimen are selectively highlighted. The cleared, stained specimen is applied to a microscope slide, cuvette, or well for observation, and optionally, is covered with a cover slip. The stain or dye can be a fluorescent stain or dye, so that the cleared stained specimen can be visualized using a fluorescent and/or epifluorescent and/or confocal microscope.

Another aspect of the application is directed to a method of preparing a specimen for spectrophotometric analysis, comprising applying a specimen to a cuvette; and applying a sufficient quantity of a clearing agent and mounting solution according to the disclosure to mount said specimen.

The disclosure also provide a method of preparing a specimen for spectrophotometric analysis wherein, before soaking the specimen in a clearing agent and mounting solution, a stain or dye is applied to the specimen to provide a stained specimen, whereby the features of the specimen are selectively highlighted. The stained specimen is then soaked in the clearing solution according to the disclosure for at least about 1 minute to about 12 months to provide a cleared, stained specimen. The cleared, stained specimen is applied to a microscope slide, cuvette, or well for observation, and optionally, is covered with a cover slip. The stain or dye can be a fluorescent stain or dye, so that the cleared stained specimen can be visualized using a fluorescent and/or epifluorescent and/or confocal microscope.

In still another aspect, the disclosure is directed to use of a clearing agent and mounting solution according to the disclosure to remove pigment, dye, stain, or color from a specimen.

A further aspect of the application is directed to use of a clearing agent and mounting solution according to the disclosure to remove excess stain or dye and to increase the contrast of particular structures and/or organisms within a specimen.

Another aspect of the application is directed to use of a clearing agent and mounting solution to increase the transparency of a specimen and to allow multiple vertical planes to be visualized without the need to section, remount, or further modify the specimen.

Yet another aspect of the disclosure is directed to use of a clearing agent and mounting solution to simultaneously dehydrate, depigment, and clear specimens for microscopic and/or visual analysis.

BRIEF DESCRIPTION OF THE DRAWINGS

The foregoing and other objects of the present disclosure, the various features thereof, as well as the invention itself may be more fully understood from the following description, when read together with the accompanying drawings in which:

FIGS. 1A-1B are representations of microscopic views of a characteristic annular vessel elements and fibers of ginger, *Zingiber officinale* Roscoe (Zingiberaceae); comparison of acidified chloral hydrate solution versus Example 1 solution;

FIGS. 2A-2B are representations of microscopic views of abundant starch grains of ginger, *Zingiber officinale* Roscoe (Zingiberaceae); comparison of acidified chloral hydrate solution versus Example 1 solution;

FIGS. 3A-3B are representations of microscopic views of ginger epidermis and parenchyma cells, *Zingiber officinale* Roscoe (Zingiberaceae); comparison of acidified chloral hydrate solution versus Example 1 solution;

FIGS. 4A-4B are representations of microscopic views of fragments of epidermis over leaf veins, Mate (leaves), *Ilex paraguariensis* (Aquifoliacea); comparison of acidified chloral hydrate solution versus Example 1 solution;

FIGS. 5A-5B are representations of microscopic views of the upper epidermis underlying palisade cells, Mate (leaves), *Ilex paraguariensis* (Aquifoliacea); comparison of acidified chloral hydrate solution versus Example 1 solution;

FIGS. 6A-6B are representations of microscopic views of fragments or groups of pericycle of fibers, Mate (leaves), *Ilex paraguariensis* (Aquifoliacea); comparison of acidified chloral hydrate solution versus Example 1 solution;

FIGS. 7A-7B are representations of microscopic views of the lower epidermis showing characteristic anomocytic stomata, Mate (leaves), *Ilex paraguariensis* (Aquifoliacea); comparison of acidified chloral hydrate solution versus Example 1 solution;

FIGS. 8A-8B are representations of microscopic views of rounded or elliptical pollen grains with three germinal pores, exine (outermost cell wall of pollen grain) dentate spinose, Safflower (flower), *Carthamus tinctorius* L. (Asteraceae); comparison of acidified chloral hydrate solution versus Example 1 solution;

FIGS. 9A-9B are representations of microscopic views of laticiferous ducts (tubular cells containing latex fluid) with a reddish-brown secretion next to vessels elements, Safflower (flower), *Carthamus tinctorius* L. (Asteraceae); comparison of acidified chloral hydrate solution versus Example 1 solution;

FIGS. 11A-11H are representations of micrographs displaying fresh whole mounted specimens cleared with Example 1 clearing agent and mounting solution. A-B: Basil leaf; C-F: Oregano leaf; G-H: *Arabidopsis thaliana* root;

DETAILED DESCRIPTION

Figure 10:
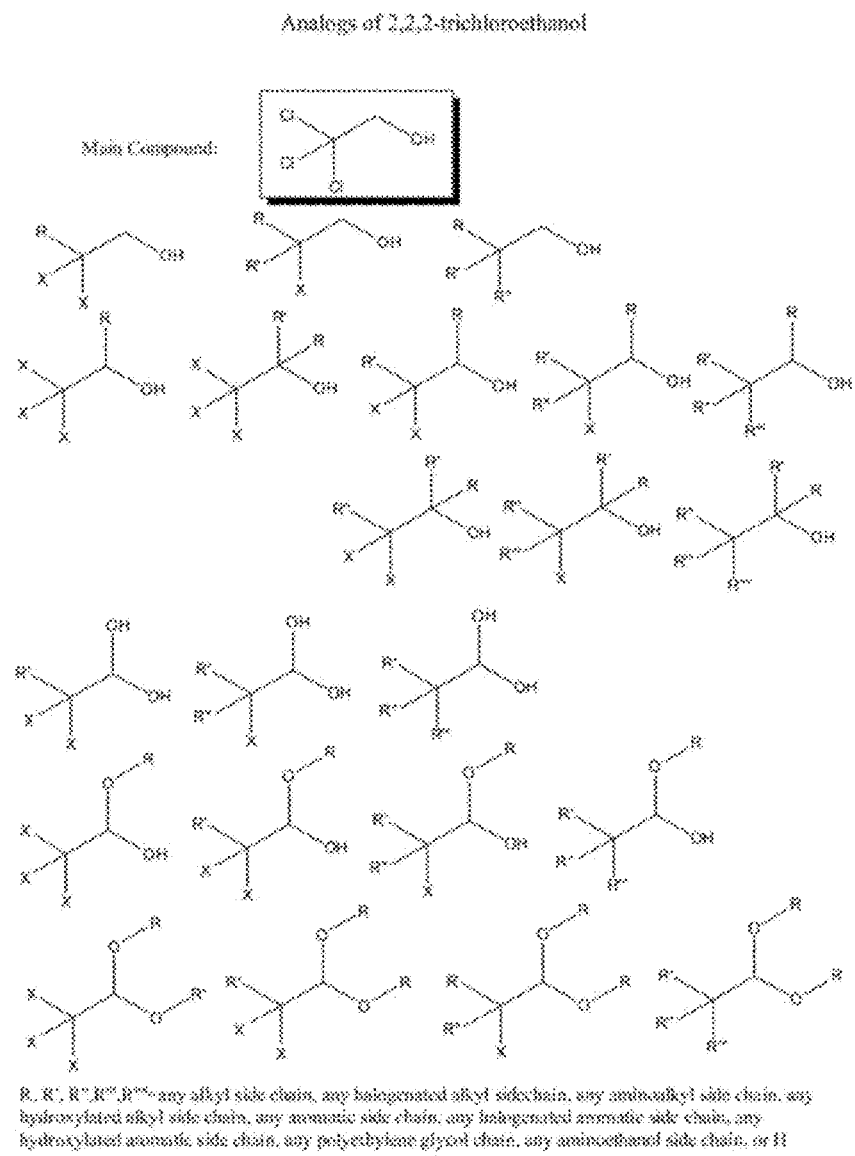
FIG. 10 is a schematic representation of the chemical structures of analogs of 2,2,2-trichloroethanol useful for preparation of clearing agent and mounting solutions of the application.

Throughout this application, various patents, patent applications, and publications are referenced. The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

For the purposes of the present disclosure, the term "stain" or "staining" includes, but is not limited to, chemical interactions between colored or fluorescent dyes and selected parts of a tissue; any method of allowing an antibody, aptamer, affibody, protein, peptide, single-stranded DNA or RNA, polysaccharide, glucosamine, dextran, lectin, or ligand, chemically conjugated to a fluorescent or colored molecule, to interact and bind to a tissue; any method of allowing an antibody, aptamer, affibody, protein, peptide, single-stranded DNA or RNA, polysaccharide, glucosamine, dextran, lectin, or ligand, chemically conjugated to a binding-site ligand (such as, but not limited to, biotin) to interact and bind to a tissue, and subsequent treatment with a protein conjugated to a colored or fluorescent molecule which binds the conjugated ligand with high affinity (such as, but not limited to, streptavidin); any method of allowing an antibody, aptamer, affibody, protein, peptide, single-stranded DNA or RNA, polysaccharide, glucosamine, dextran, lectin, or ligand, chemically conjugated to a reactive enzyme to interact and bind to a tissue, which becomes optically active upon subsequent treatment with the substrate of the reactive enzyme conjugated to a colored or fluorescent molecule; any method of allowing an antibody, aptamer, affibody, protein, peptide, single-stranded DNA or RNA, polysaccharide, glucosamine, dextran, lectin, or ligand, chemically conjugated to a reactive molecular moiety (such as, but not limited to, 1-ethynl) to interact and bind to tissue, and which becomes optically active upon subsequent treatment with a colored or fluorescent molecule conjugated to a molecular moiety (such as, but not limited to, azido) that can react with the conjugate to form a covalent linkage; any method of allowing an antibody, aptamer, affibody, protein, peptide, single-stranded DNA or RNA, polysaccharide, glucosamine, dextran, lectin, or ligand, chemically conjugated to a single strand or DNA/RNA or DNA/RNA derivatives, to interact and bind with the tissue, and which becomes optically active upon subsequent treatment with the antisense DNA/RNA/derivative conjugated to a colored or fluorescent molecule.

It has now been discovered that aqueous solutions of trichloroethanol, and/or its derivatives or analogs, with certain other additives, can effectively replace acidified chloral hydrate solution as a clearing and mounting medium for microscopy for both living and nonliving organisms and nonliving materials. These solutions can be used as non-chloral hydrate clearing and mounting compounds of appropriate refractive index for novel applications in microscopy. Given the current shortage and limitation of access to the commercial universally-used clearing agent (acidified chloral hydrate), the present disclosure provides to consumers and the general public a method that can replace the currently used clearing agent, and provides a method accessible to those who are no longer able to purchase the regulated compound chloral hydrate. Thus, the clearing reagents and methods of the present disclosure are of immediate commercial value and of significant impact because both scientists and manufacturers have been seeking to find a replacement for chloral hydrate in microscopy and other optical applications. The clearing reagents and methods of the present disclosure are also of immediate commercial value and of significant impact because they can be used with many stains as well as for semi-permanent and permanent mounting.

The present disclosure provides a substitute for acidified chloral hydrate glycerol solution, wherein the solution components, for example trichloroethanol, are inexpensive, easy to acquire, do not require a DEA license to possess and use, and greatly reduce the risk involved in operations which formerly depended on the use of chloral hydrate. The solutions according to the disclosure possess a high refractive index (greater than or equal to about 1.3810; about 1.3810 to about 1.4880; or about 1.4315 to about 1.4880. For example, it can be higher than acidified chloral hydrate solution (1.4280), which results in clearer, and equivalent or higher quality viewing under a microscope. High refractive indices are required for clear viewing of objectives in microscopy, as materials with a high refractive index are more transparent. As a reference, the refractive index of borosilicate (Pyrex) glass is 1.470. In more examples, the clearing agent and mounting solution of the disclosure have refractive indices higher than that of glass. It has been discovered that trichloroethanol, or its derivatives or analogs, admirably meet the above-identified criteria as replacements for chloral hydrate.

Use of the clearing agent and mounting solution of the disclosure helps to macerate and digest clusters of cellular material, and helps to clarify and increase transparency of those tissues, minerals, elements of interest in microscope slides. This solution is an effective immersion medium, and useful in all types of fixative preparations and as an effective dehydration agent. The clearing compound and/or its derivatives can also be used as a semi-permanent or permanent mount, allowing one to visualize specimens days or even months later. This clearing compound and/or its derivatives can also be used with many stains, allowing one to further visualize specimens and components within specimens.

1. Clearing Agent and Mounting Solutions

This disclosure encompasses the identification of chemical compounds and combinations thereof that have not heretofore been used in microscopy applications. In one representation example, the clearing agent and mounting solution of the disclosure comprises any concentration of 2,2,2-trichloroethanol, or derivatives or analogs thereof, and/or 2,2,2-trichloroacetic acid, or derivatives or analogs thereof in water and/or glycerol and/or alcohol solution, mixed for the purpose of clearing and/or mounting media for microscope/optical use.

The clearing agent and mounting solution may alternatively comprise, in addition to TCE and/or its derivatives, benzyl alcohol, benzyl benzoate, and/or benzyl ether. In addition, the clearing agent and mounting solution described above may contain ethylene glycol (EG), polyethylene glycol (PEG), and/or propylene glycol (PG), and/or derivatives thereof such as, but not limited to, glycol ethers, alkyl diols, alkyl triols, alkyl polyols, and other poly-alkoxy-hydroxy ethers, including, but not limited to, diethylene glycol, dipropylene glycol, triethylene glycol, 1,3-propanediol, 1,4-butanediol, 1,5-pentanediol, 2(2-ethoxyethoxy)ethanol, bis (2-methoxyethyl) ether, 2(2-butoxyethoxy)ethanol, PEG 200, PEG 400, and/or PEG 600.

For the purposes of the present disclosure, the term "derivative" encompasses a chemical compound which still retains the parent structure as a substructure, and can be chemically derived from the parent (e.g., trichloroethanol or trichloroacetic acid). For example, with 2,2,2-trichloroethanol as the parent, a derivative would retain the 2,2,2-trichloroethoxy substructure, such as is found in the corresponding acetate (1-acetoxy-2,2,2-trichloroethane, alternatively named 2,2,2-trichloroethylacetate) or the methyl ether (1-methoxy-2,2,2-trichloroethane) derivatives.

Also for the purposes of the present disclosure, the term "analog" encompasses a chemical compound in which the core structure of the parent is changed or further substituted, as is commonly known in the medicinal chemistry arts. For example, the change can include replacement of atoms or groups with other atoms or groups (isosteres). Non-limiting examples of analogs of 2,2,2-trichloroethanol are displayed in FIG. 10.

The clearing agent and mounting solution of the disclosure comprises trichloroethanol and/or its analogs or derivatives. It may also comprise both trichloroethanol and/or its derivatives or analogs, and trichloroacetic acid and/or derivatives or analogs. For example, the clearing agent and mounting solution may comprise about 5% to about 97% (v/v) trichloroethanol or derivatives thereof; 0% to about 50% (v/v) trichloroacetic acid; 0% to about 50% (v/v) glycerol; and optionally, water; wherein the refractive index of said clearing agent and mounting solution is greater than or equal to about 1.3810, or about 1.3810 to about 1.4880, or about 1.4315 to about 1.4880. The clearing agent and mounting solution can optionally further contain a C1-C6 alcohol, another acid, such as hydrochloric acid, and/or a dye or stain for visualizing various components of the specimen. In one aspect, trichloroethanol is present in about 34.5% to about 97%. In another non-limiting example, trichloroacetic acid is present in 0% to about 5%. For example, glycerol can be present in about 0% to about 12.5%. The glycerol can be supplemented or replaced entirely with one or more compounds selected from the group consisting of ethylene glycol, propylene glycol, polyethylene glycols and/or derivatives thereof.

In other examples, the clearing agent and mounting solution comprises about 34.5% to about 97% trichloroethanol, 0% to about 5% trichloroacetic acid, and 0% to about 12.5% glycerol, or about 56.25% (v/v), trichloroacetic acid in about 1.25% (v/v), glycerol in about 12.5% (v/v), methanol in about 25%, and water in about 5% (v/v).

A further example of the clearing agent and mounting solution of the disclosure comprises trichloroacetic acid and/or derivatives without trichloroethanol and/or derivatives. One example of the clearing agent and mounting solution consists of an aqueous glycerol solution of trichloroethanol and trichloroacetic acid (Example 1). The trichloroacetic acid can be supplemented or replaced entirely with hydrochloric acid and/or sulfuric acid. One example of the clearing agent and mounting solution consists of an aqueous glycerol solution of trichloroethanol and hydrochloric acid. The 2,2,2-trichloroethanol analog, 2-chloroacetaldehyde dimethyl acetal, FIG. 10, also serves as an effective clearing agent. The clearing agent and mounting solution can include derivatives of 2,2,2-trichloroethanol and/or 2,2,2-trichloroacetic acid created by adding/adjusting the concentration of buffer, and/or acidic/basic additives intended to alter pH and/or salt concentration of the solution; and/or compounds to increase/decrease the digestive capacity of the reagent;

and/or any additives intended to preserve specimens/samples; and/or any additives intended for dying or staining applications.

With regard to the alcohol (other than trichloroethanol or derivatives), the clearing agent and mounting solutions can comprise one or more C1-C6 alcohols, for example ethanol, 1-propanol, 2-propanol or t-butanol.

The clearing agent and mounting solutions can also further comprise a dissolved plastic polymer, such as polyvinylpyrrolidone, polypropylene, polyethylene, polyether, polyamide; and/or monomeric units which are subsequently polymerized in order to stabilize a mounting medium and/or specimen; and/or one or more C1-C12 organic acids, such as formic acid, acetic acid, lactic acid, ascorbic acid, gallic acid, benzoic acid, toluic acid, p-hydroxybenzoic acid or citric acid; and/or a chemical preservative; and/or a salt of phosphate, citrate, acetate, tris, or other water-soluble buffers; the buffer can be added as an aqueous solution; and/or alkaline hydroxide base, such as sodium hydroxide, calcium hydroxide or lithium hydroxide; the base can be added as an aqueous solution. The inventive clearing agent and mounting solution and/or its derivatives and/or its analogs can also be used with commercial and noncommercial stains just as effectively as current clearing agents.

The present disclosure also encompasses various derivatives and/or analogs of 2,2,2-trichloroethanol including mono- or poly-halogenated branched or unbranched alcohols, diols, glycols, aldehydes, aldehyde-hydrates, hemiacetals, acetals, ketals, aminals, and hemi-aminals of at least 2 carbon units, where branches are defined as any mono- or poly-halogenated aliphatic or aromatic side chains containing hydroxyl, amino, ether, carboxyl, carboxyamido, carbonate, carbamyl, carbonyl-chloride, polyethyleneglycol, or aminoethanol groups, and any polymeric embodiment of such derivatives. Derivatives and analogs of 2,2,2-trichloroacetic acid include mono- or poly-halogenated branched or unbranched carboxylic acids, carbamates, amides, and carbonates of at least 2 carbon units, where branches are defined as any mono- or poly-halogenated aliphatic or aromatic side chains containing hydroxyl, amino, ether, carboxyl, carboxyamido, carbonate, carbamyl, carbonylchloride, polyethylene-glycol, or aminoethanol groups, and any polymeric embodiment of such derivatives.

Other examples of the clearing agent and mounting solution comprises about 10% to about 97% (v/v) of a trichloroethanol derivative or analog; 0% to about 50% (v/v) of a trichloroacetic acid derivative or analog; 0% to about 50% (v/v) of glycerol; and optionally, water; wherein the refractive index of said solution is greater than or equal to about 1.3810; wherein the trichloroethanol derivative or analog is mono- and poly-halogenated branched and unbranched alcohols, diols, glycols, aldehydes, aldehyde-hydrates, hemiacetals, acetals, ketals, aminals, and hemi-aminals of at least 2 carbon units, and any polymeric embodiment of such derivatives, and where branches are defined as any mono- or poly-halogenated aliphatic or aromatic side chains containing hydroxyl, amino, ether, carboxyl, carboxyamido, carbonate, carbamyl, carbonyl-chloride, polyethylene-glycol, or aminoethanol groups.

2. Optical Properties of the Solutions

The disclosure provides a solution which increases the apparent transparency of an objective in microscopy/optical techniques by increasing the refractive index of the medium in which said objective is suspended/immersed. Refractive index of a material is a dimensionless quantity which represents the way light propagates through the material. The refractive index is defined as the factor by which the wavelength and the velocity of the radiation with respect to in a vacuum. The refractive index of a material is closely related to its dielectric constant, and therefore to its transparency. The refractive index n of a material is given by the following equation:

$$n = \sqrt{\frac{\sqrt{\epsilon_1^2 + \epsilon_2^2} + \epsilon_1}{2}},$$

where $\epsilon_1$ and $\epsilon_2$ represent the real and imaginary parts of the dielectric constant, respectively. Materials which have a high dielectric constant contain multiple lone pairs of electrons and/or electronegative elements, which give them a high degree of polarizability, the property which is expressed by the dielectric constant. A high degree of polarizability allows for an electromagnetic wave to propagate easily through the material, since as the electromagnetic wave propagates through the material, it will induce a localized electromagnetic field. It is useful to use the analogy of waves through liquids, the less viscous and easier the liquid is to move (by analogy related to higher polarizability), the easier a wave can propagate through without losing energy from absorption. In electromagnetic waves, a high polarizability corresponds to this "easier movement" of the wave through the material, which results in less absorption of the wave by the material. Therefore, materials with high dielectric constants will have a low degree of absorption, and therefore a high degree of transparency, as the objective light will make it through the material without absorption loss. Effectively, the photons of light can escape more unscathed than they would in a material with a lower dielectric constant. And since dielectric constant is related to refractive index as shown above, materials with a high refractive index will also be highly transparent, and therefore of great use in microscopy/optical techniques.

Refractive indices of exemplary clearing agent and mounting solutions of the disclosure are disclosed in Table 1.

TABLE 1

| Clearing Agent and Mounting Solution Formulation[1] Composition (v/v)% | Refractive Index (nD20) |
|---|---|
| TCE-34.5%; Glyc-12%; HCl (34%)-1.5%; H$_2$O-28%; MeOH-24% | 1.4155 |
| TCE-45%; Glyc-10%; HCl-1.25%; H$_2$O-23.75%; MeOH-20% | 1.4310 |
| TCE-27.4%; Glyc-8.3%; TCAA-0.7%; MeOH-14.2%; LA-49.4% | 1.4370 |
| TCE-56.25%; Glyc-12.5%; TCAA-1.25%; H$_2$O-30% | 1.4315 |
| TCE-27.4%; Glyc-8.3%; TCAA-0.7%; MeOH-14.2%; DMSO-49.4% | 1.4640 |
| TCE-94%; TCAA-5%; NaOH-1% | 1.4880 |
| TCE-91%; Glyc-3.3%; TCAA-0.3%; MeOH-5.4% | 1.4875 |
| TCE-27.4%; Glyc-8.3%; TCAA-0.7%; MeOH-14.2%; Tol-49.4% | 1.4770 |
| TCAA-6%; NaOH-4%; H$_2$O-90% | 1.4280 |
| TCE-97%; TCAA-3% | 1.4885 |
| TCE-63.0%; Glyc-13.2%; TCAA-1.1%; MeOH-22.7% | 1.4565 |
| TCE-27.4%; Glyc-8.3%; TCAA-0.7%; MeOH-63.6% | 1.3895 |
| TCE-27.4%; Glyc-8.3%; TCAA-0.7%; MeOH-14.2%; CWO-49.4% | 1.4790 |
| TCE-54.8%; Glyc-16.6%; TCAA-1.4%; MeOH-27.2% | 1.4450 |
| 36% TCE + 36% BA + 27% Glyc | 1.5075 |
| 33% TCE + 33% BA + 33% Glyc | 1.5021 |
| 33% TCE + 33% BA + 17% Glyc + 17% BB | 1.5202 |
| 29% TCE + 29% BA + 17% Glyc + 13% BB + 13% BE | 1.5236 |

TABLE 1-continued

| Clearing Agent and Mounting Solution Formulation[1] Composition (v/v)% | Refractive Index (nD20) |
|---|---|
| 42% TCE + 16.5% BA + 16.5% Glyc + 25% BE | 1.5145 |
| 10% TCE + 90% BA | 1.5355 |
| 90% TCE + 10% BA | 1.4951 |
| 10% TCE + 90% BB | 1.5614 |
| 90% TCE + 10% BB | 1.4984 |
| 33% TCE + 33% BA + 33% BB | 1.5331 |
| 10% TCE + 90% BE | 1.5550 |
| 50% TCE + 50% BE | 1.5255 |
| 90% TCE + 10% BE | 1.4972 |

[1]TCE = trichloroethanol,
CAA = trichloroacetic acid,
Glyc = glycerol,
MeOH = methanol,
NaOH = sodium hydroxide,
LA = lactic acid,
DMSO = dimethylsulfoxide,
Tol = toluene,
CWO = cedar wood oil.
BA = benzyl alcohol
BB = benzyl benzoate
BE = benzyl ether A number of analog structures have been provided which can be used as a substitute for trichloroethanol (FIG. 10). 2-chloroacetaldehyde dimethyl acetal has been shown to be effective at the same concentrations as trichloroethanol, although the refractive index is only 1.3810, at the low end of the desired range. One way to achieve the desired refractive index is to incorporate a clearing agent having one or more halogens (F, Cl, Br, I) in a carbon skeleton which also contains a water solubilizing group capable of hydrogen bonding. For example, the carbon skeletons can be selected from any mono- or poly-halogenated branched or unbranched alcohol, diol, glycol, aldehyde, aldehyde-hydrate, hemi-acetal, acetal, ketal, aminal, or hemi-aminal of C1-C20 family, where branches are defined as any mono- or poly-halogenated aliphatic or aromatic side chains containing hydroxyl, amino, ether, carboxyl, carboxyamido, carbonate, carbamyl, carbonyl-chloride, polyethylene-glycol, or aminoethanol groups, and any polymeric arrangement of such derivatives.

In comparative qualitative examinations, the clearing agent and mounting solutions of the disclosure perform as well as or better than acidified chloral hydrate. In quantitative examinations, the clearing agent and mounting solution of the disclosure has matched or outperformed the chloral hydrate-based solutions, and exhibited a refractive index greater than chloral hydrate solution, the universal standard. Thus, the clearing agent and mounting solution can be used to identify the same anatomical characteristics or diagnostic features that are employed for the identification of different plant, microbial, animal, and earth science materials, without losing clarity, definition or resolution of the objective structures.

3. Methods

The clearing agent and mounting solutions of the disclosure are useful for microscopic identification of plants, plant parts, animals and microbial materials. The clearing agent and mounting solutions can be used for visualization of any living organisms such animals, fungi, protists, and bacteria, even with blood and plasma samples, as a mounting medium in microscopy and/or other optical techniques with applications in forensics, and biology and earth sciences. These solutions can be used to clear specimens, rendering them transparent. These cleared specimens can later be differentially stained and high quality images obtained. Alternatively, uncleared specimens can be stained first and then cleared. The inventive clearing agent and mounting solutions and semi-permanent mounting media can also be used with non-living materials, including, but not limited to, soil particles and geological samples.

The inventive clearing agent and mounting solutions are useful not only for botanical microscopy but also for mycology, entomology, histology, food science, quality control (identification of living organisms for manufacture of pharmaceuticals, excipients, dietary products, adulterations, misidentifications, contaminations), forensics, nematology, virology, immunology, mineralogy, microscopy including, but not limited to, differential interference contrast microscopy, electron microscopy, and other related applications of microscopy and optics.

For example, one application of the inventive clearing and mounting solution is in quality assessment of commercial herbal products. It has also been determined that the inventive solutions are useful for clearing whole mounted dried, partially dry and fresh materials. For example, in basil, the oil glands, epidermis with stomata and underlying palisade cells could be observed (FIGS. 11A, B). In oregano, the epidermis over the vein with covering trichomes, capitates and peltate oil glands was distinguished (FIGS. 11C-F). Details of the cellular organization of the root apical meristem in *Arabidopsis thaliana* can be observed after clearing with this application (FIGS. 11G-H). In addition, a number of other herbs and spices (dry samples and whole tissues) were analyzed subsequently using the disclosure as clearing reagent with comparable results.

The solutions of the disclosure penetrate into tissues and render them more transparent, as does acidified chloral hydrate solution. After treatment with a clearing agent of the disclosure, samples are cleared, which allows internal as well as surface details to be easily identified. This feature is useful with whole mount tissues in which different layers of the transparent tissues are observed without the need for sectioning or remounting. Clear tissues also allow for staining techniques to more effectively highlight diagnostic features in only one single step without requiring dehydration of the tissues or pre-treatment of the tissues (FIGS. 11A-H).

Figure 14:
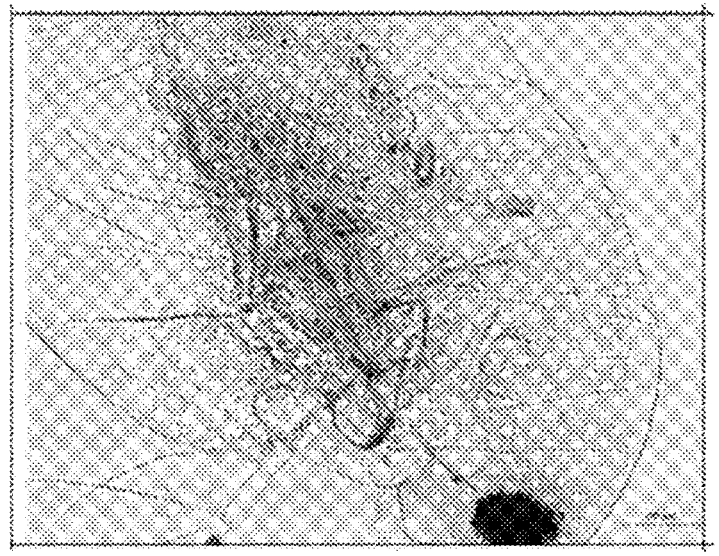
FIG. 14 is a representation of a micrograph of a small aquatic crustacean *Daphnia* sp. (Animalia) anterior end showing internal structures, cleared with Example 1 clearing agent and mounting solution.
Figure 15:
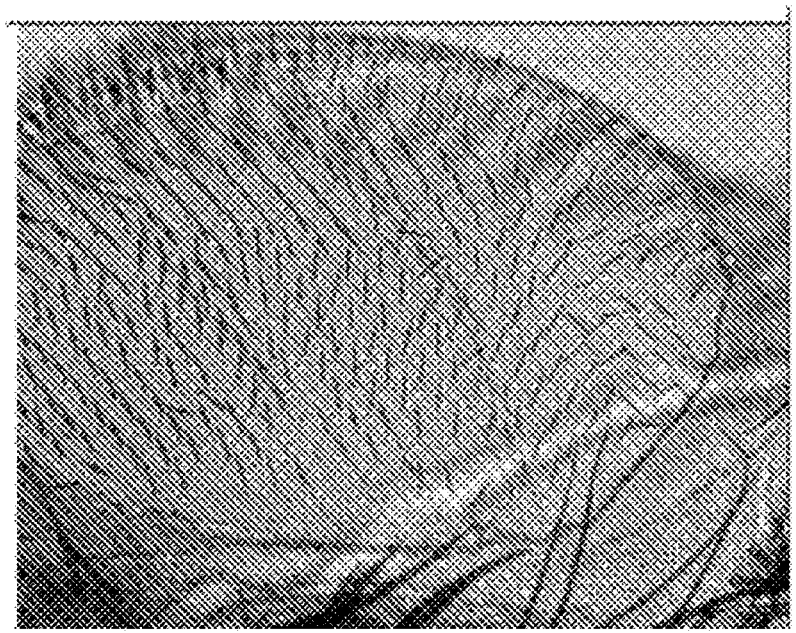
FIG. 15 is a representation of a micrograph of a characteristic *Drosophila melanogaster* (Animalia) compound eye, cleared with Example 1 clearing agent and mounting solution.
Figure 16:
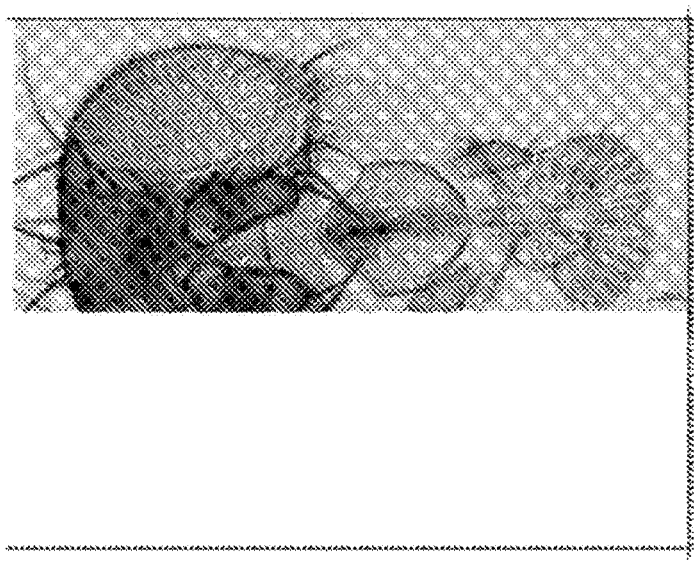
FIG. 16 is a representation of a micrograph of a dorsal view of the head of *Drosophila melanogaster* (Animalia) showing compound eye, antenna and mouth parts, cleared with Example 1 clearing agent and mounting solution.

The inventive solutions are also effective to clear protists, animals including, but not limited to, red algae (FIG. 12), round worms (*Panagrellus redivivus*, FIG. 13), water fleas, *Daphnia* sp (FIG. 14), and fruit flies (*Drosophila melanogaster*, FIGS. 15 and 16).

In order to identify different components in the cells, tissues can be stained. There are several staining combinations available to enhance the details between different components of the cells. Stains are selected to provide the maximum contrast between particular structures based on their chemical composition. Much of the success of the images obtained after staining is due to the clearing agent used as a pretreatment. The solutions of the present disclosure also have no interference with the major stains used for particular structures. As examples, *penicillium* sp was first cleared with a clearing agent and then stained with a solution of aniline blue in lactic acid (FIG. 17), downy mildew became dark brown after staining with iodine solution and sulfuric acid (FIG. 18), the round worm *Pangrellus redivivus* stained pink/red with fuchsine (FIG. 19), starch grains were stained black with iodine solution in ginger rhizome dry samples (FIG. 20) and sclereids fibers were stained red with phloroglucinol/HCl solution (FIG. 21).

The disclosure is also directed to a method of preparing a biological specimen (e.g., plant, animal, etc.) for microscopy. One example of such a method comprises applying a specimen to be examined to a microscope slide, well, or cuvette; applying a sufficient quantity of the clearing agent and mounting solution to clear and mount said specimen; and optionally, applying a cover slip. For example, about 1 drop to about 100 drops, or about 2 drops of the clearing agent and mounting solution are applied to the specimen on the slide in order to fix/mount the specimen. The specimen can be further protected with a cover slip.

The disclosure also provides a method of preparing a specimen for spectrophotometric analysis. In this method a specimen is applied to a cuvette or well, and a sufficient quantity of the clearing agent and mounting solution according to the disclosure is applied to clear the specimen, e.g., about 1×-10× volume of sample.

In an alternative method, the specimen is stained before being cleared. More specifically, before soaking the specimen in a clearing solution, a stain or dye is applied to the specimen to provide a stained specimen, whereby the features of the specimen are selectively highlighted. The stained specimen is then soaked in the clearing solution according to the disclosure for a sufficient amount of time to provide a cleared, stained specimen, e.g., at least about 1 minute to about 12 months. The cleared, stained specimen is applied to a microscope slide, cuvette, or well for observation, and optionally, is covered with a cover slip. The stain or dye can be a fluorescent stain or dye, so that the cleared, stained specimen can be visualized using a fluorescent and/or epifluorescent and/or confocal microscope.

Reference will now be made to specific examples illustrating the disclosure. It is to be understood that the examples are provided to illustrate exemplary embodiments and that no limitation to the scope of the disclosure is intended thereby.

EXAMPLES

Example 1

Preparation of Plant Specimens

Plant materials were dried or used fresh. Dried plant materials were ground to a fine powder using a commercial coffee grinder.

A small quantity of fine powder material was spread on a microscope slide, and mounted with two drops acidified chloral hydrate solution (control), or mounted with two drops of the clearing agent and mounting solution of Example 1 and a cover slip was attached. Then the slide was heated on a hot plate (medium temperature) for 30 sec-60 sec until the clearing agent and mounting solution boiled. The microscopic analysis was conducted using a Nikon eclipse 80i microscope, with the imaging software NIS D 3.00 SP7. Differences or similarities in diagnostic features or characteristics for each sample were recorded. Fresh specimens were submerged in the clearing agent and mounting solution until they were transparent, usually taking around 20-30 minutes depending the thickness of the material. Larger samples may require up to 2-3 days. Once the material was cleared, it was mounted on a microscope slide with one or two drops of this disclosure and a cover slip was added. Fresh specimens were cleared and transparent, allowing the visualization of deeper layers of tissues without losing clarity.

For staining the materials, first the material was cleared as described above, the cover slip was removed, one or two drops of the stain was added, and after a few minutes a cover slip was reapplied.

Example 2

Preparation of a Clearing Agent and Mounting Solution 4.5 mL of 2,2,2-trichlorethanol (Sigma-Aldrich, 99%, reagent grade) was thoroughly mixed with 1.0 mL of glycerol. To this homogenous solution was added 2.5 mL of a 4% (m/v) aqueous solution of 2,2,2-trichloroacetic acid, at which time cloudiness was observed. The solution was mixed thoroughly until completely clear, about 5 min.

Example 3

Ginger (Rhizome), *Zingiber officinale* Roscoe (Zingiberaceae)

Powdered ginger samples are characterized by numerous fragments of isodiametric thin-walled parenchyma cells containing starch granules; fragments of thin-walled fibers with oblique slit-like pits; fragments of scalariform, reticulate, and spiral vessels; thin-walled cells with suberized radial walls; numerous starch granules with various forms such as simple, flat, oval, oblong with terminal protuberance.

In ground ginger samples, fragments of parenchyma cells, cell with circular striations (cork cells), fibers accompanied by vessels and abundant starch grains the compact epidermal cells with sharp edges can be observed using the clearing agent and mounting solution of the disclosure. There was no difference in the structures observed between the inventive and standard clearing agent and mounting solutions.

FIGS. 1A-B show microscopic views of characteristic annular vessel elements and fibers of ginger: FIG. 1A, ginger characteristic annular vessel element and fibers using acidified chloral hydrate solution; FIG. 1B, ginger characteristic annular vessel element with fibers and abundant starch grains attached to the fibers using clearing agent and mounting solution of Example 1.

FIGS. 2A-B show microscopic views of abundant starch grains of ginger. More starch grains can be observed using the clearing agent and mounting solution of Example 1, versus acidified chloral hydrate solution: FIG. 2A, ginger sample with characteristic abundant starch granules, mostly simple, using acidified chloral hydrate solution; FIG. 2B, ginger sample with abundant starch grains using clearing agent and mounting solution of Example 1.

FIGS. 3A-B show microscopic views of ginger epidermis and parenchyma cells. There is no difference in the structures observed using the inventive solution, versus acidified chloral hydrate solution: FIG. 3A, group of compact epidermal cells using acidified chloral hydrate solution; FIG. 3B, group of compact epidermal cells using clearing agent and mounting solution of Example 1.

Example 4

Mate (Leaves), *Ilex paraguariensis* (Aquifoliacea)

Ground Ilex leaves are characterized by upper epidermis composed by polygonal cells with unevenly thickened walls. Lower epidermis cells are smaller than those of the upper epidermis, and thinner cell walls, cuticular striations are well marked. Stomata anomocytic (epidermal cells surrounding the guard cell pair are not morphologically distinct from the other epidermal cells). Groups of lignified fibers are visible.

FIGS. 4A-B show microscopic views of fragments of epidermis over leaf veins. The upper epidermis is composed of polygonal cells with unevenly thickened walls. Stomata are absent in the upper epidermis. There are no differences observed using the inventive solution, versus acidified chloral hydrate solution: FIG. 4A, fragment of polygonal cells of the upper epidermis over the vein using acidified chloral hydrate solution; FIG. 4B, fragments of polygonal cells of the upper epidermis over the vein using clearing agent and mounting solution of Example 1.

FIGS. 5A-B show microscopic views of the upper epidermis underlying palisade cells, large and closely packed. Circular striations can be observed. Those cells treated with the invented solution are less obscured versus those treated with acidified chloral hydrate solution: FIG. 5A, fragment of upper epidermis underlying parenchyma cells, cuticle is irregular striated, using acidified chloral hydrate solution; FIG. 5B, fragment of upper epidermis underlying parenchyma cells, cuticle is irregular striated, using clearing agent and mounting solution of Example 1.

FIGS. 6A-B show microscopic views of fragments or groups of pericycle of fibers. Fibers are lignified, moderately thickened and have pitted walls (gap in the internal secondary thickening of the cell wall). Pits from the fibers in FIGS. 6A and 6B can be clearly observed with both clearing agent and mounting solutions: FIG. 6A, longitudinal view of a vein section showing fibers which have thickened walls with rounded or slit shaped pit (gap in the internal secondary thickening of the cell wall), using acidified chloral hydrate solution; FIG. 6B, longitudinal view of a vein section showing fibers which have thickened walls with rounded or slit shaped pit (gap in the internal secondary thickening of the cell wall), using clearing agent and mounting solution of Example 1.

FIGS. 7A-B show microscopic views of the lower epidermis showing characteristic anomocytic stomata. There was no difference between the clearing agent and mounting solutions in clarity and function: FIG. 7A, lower epidermis surface showing anomocytic stomata and circular cuticular striations, using acidified chloral hydrate solution; FIG. 7B, lower epidermis surface showing anomocytic stomata and circular cuticular striations, using clearing agent and mounting solution of Example 1.

Example 5

Safflower (Flower), *Carthamus tinctorius* L. (Asteraceae)

Powdered samples of flowers from Safflower have the abundant pollen grains with three noticeable germinal pores. The exine (outer coat of the pollen grain) is dentate and spinose. The presence of laticferous ducts with a reddish brown secretion next to vessels was observed. In ground samples of safflower, pollen grains with three germinal pores, exine and laticiferous ducts with a reddish-brown secretion next to vessels could be observed.

FIGS. 8A-B show microscopic views of rounded or elliptical pollen grains with three germinal pores, exine (outermost cell wall of pollen grain) dentate spinose: FIG. 8A, characteristic pollen grain with three germinal pores, exine dentate, using acidified chloral hydrate solution; FIG. 8B, characteristic pollen grain with three germinal pores, exine dentate, using clearing agent and mounting solution of Example 1.

FIGS. 9A-B show microscopic views of laticiferous ducts (tubular cells containing latex fluid) with a reddish-brown secretion next to vessels elements. There were no differences observed using clearing agent and mounting solution, versus acidified chloral hydrate solution: FIG. 9A, two laticiferous ducts with a darker secretion next to the vessel elements, using acidified chloral hydrate solution; FIG. 9B, laticiferous duct filled with a darker secretion next to the vessel elements, using clearing agent and mounting solution of Example 1.

FIGS. 11A-H display fresh whole mounted plant specimens cleared with Example 1 clearing agent and mounting solution. FIGS. A-B: Basil leaf. FIG. A, epidermis with diacytic stomata, capitate and peltate glands; FIG. B: mesophyll cells with chloroplasts; FIGS. C-F: Oregano leaf; FIG. C, covering trichomes with thick cell walls over the vein and capitate glands; FIG. D, Close up of capitate glands (arrow); FIG. E: depicting epidermis and peltate oil gland; FIG. F: mesophyll cells; FIGS. G-H: *Arabidopsis thaliana* root; FIG. G, root tip cellular differentiation; FIG. H: xylem differentiation in root.

The clearing and mounting solution and its derivatives and/or analogs can also be used effectively in the same or a similar manner with cells or tissues from animals including, without limitation, poultry, humans, livestock, reptiles, amphibians, insects and mites, as well as protists, mold, fungi, bacteria, and other microorganisms. For mammals, vertebrates, and invertebrates, specific portions can be prepared for visualization, such as brain, spinal cord, skeletal system, etc.

The specimens displayed in FIGS. 12-21 were prepared analogously to those above, using the clearing and mounting solution of Example 1.

Figure 12:
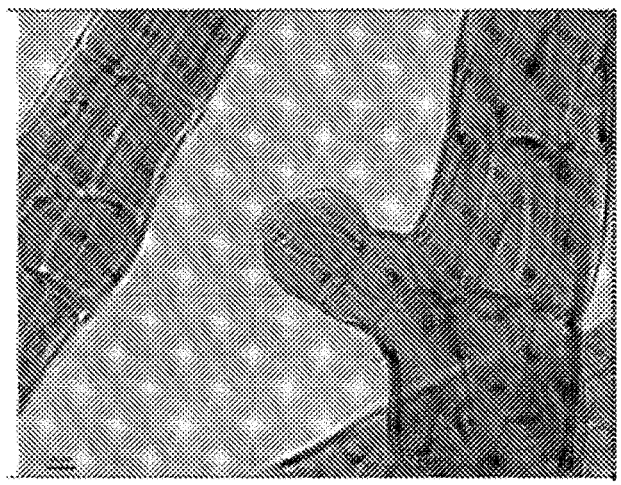
FIG. 12 is a representation of a micrograph of a red alga *Polysiphonia* sp gametophyte showing a secondary branch forming off the main axis, cleared with Example 1 clearing agent and mounting solution.

FIG. 12 shows a red alga *Polysiphonia* sp gametophyte showing a secondary branch forming off the main axis.

Figure 13:
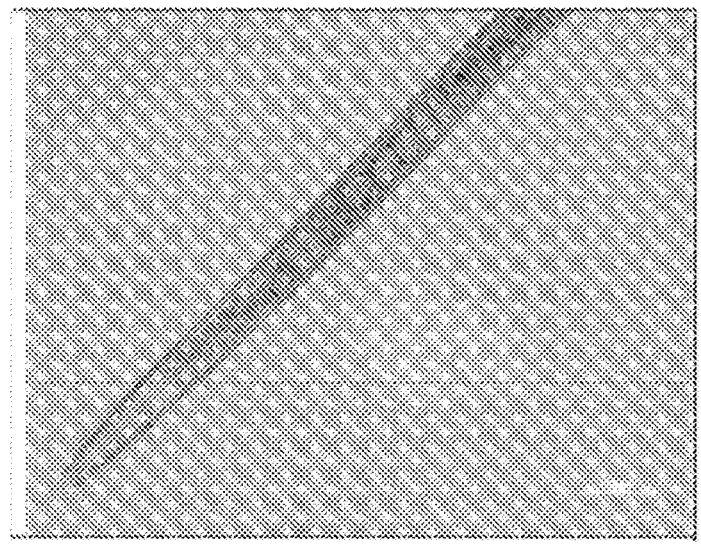
FIG. 13 is a representation of a micrograph of a roundworm free living nematode *Panagrellus redivivus* (Animalia) anterior end showing internal structures, cleared with Example 1 clearing agent and mounting solution.

FIG. 13 shows round worm free living nematode *Panagrellus redivivus* (Animalia) anterior end showing internal structures (buccal cavity and juveniles hatched internally).

FIG. 14 shows a small aquatic crustacean *Daphnia* sp. (Animalia) showing anterior section.

FIG. 15 shows characteristic *Drosophila melanogaster* (Animalia) compound eye, showing numerous ommatidia (light detectors).

FIG. 16 shows a dorsal view of the head of *Drosophila melanogaster* (Animalia) showing compound eye, antenna and mouth parts.

Figure 17:
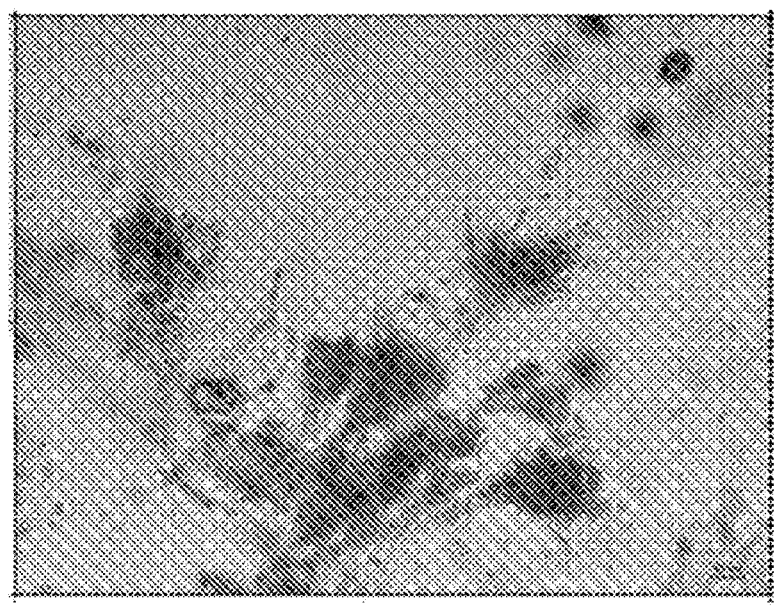
FIG. 17 is a representation of a micrograph of the fungus *Penicillium* sp. conidiophores with a chain of conidia (asexual spores) at the end, cleared with Example 1 clearing agent and mounting solution.

FIG. 17 shows fungus *Penicillium* sp. conidiophores with a chain of conidia (asexual spores) at the end.

Figure 18:
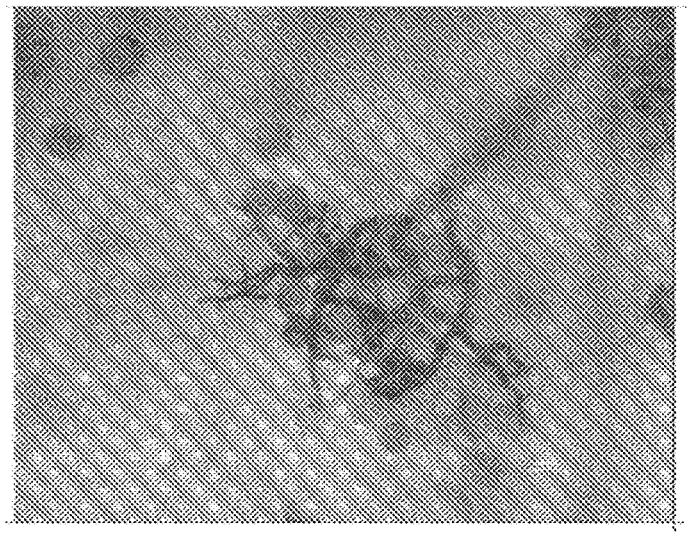
FIG. 18 is a representation of a micrograph of a basil downy mildew (*Peronospora belbahrii*), stained with iodine solution and sulfuric acid, cleared with Example 1 clearing agent and mounting solution.

FIG. 18 shows basil downy mildew (*Peronospora belbahrii*), protist, with distinct staining of characteristic branched conidiophores and conidia after one week of inoculation. Stained with iodine solution and sulfuric acid.

Figure 19:
FIG. 19 is a representation of a micrograph of a roundworm *Panagrellus redivivus* (Animalia.) stained with fuchsine, cleared with Example 1 clearing agent and mounting solution.

FIG. 19 shows a round worm *Panagrellus redivivus* (Animalia) stained with fuchsine.

Figure 20:
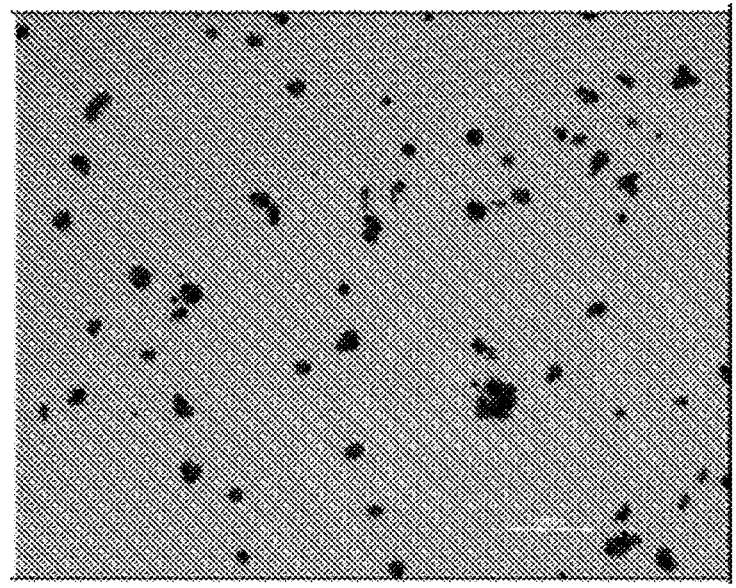
FIG. 20 is a representation of a micrograph of characteristic starch grains of Ginger (*Zingiber officinale*) stained with iodine solution, cleared with Example 1 clearing agent and mounting solution.
Figure 21:
FIG. 21 is a representation of a micrograph of characteristic lignified fibers of *Prunus africana* stained with phloroglucinol/HCl solution, cleared with Example 1 clearing agent and mounting solution.

FIG. 20 shows characteristic starch grain of Ginger stained with iodine solution.

FIG. 21 shows characteristic lignified fiber of *Prunus africana* stained with phloroglucinol/HCl solution.

Example 6

Mouse Specimens

A mouse was euthanized by cervical dislocation and immediately processed for necropsy. The brain was removed and placed immediately into 10% neutral buffered formalin. It was then left at RT for approximately 3 hr, and stored at 4° C. for 2 d. The brain was then sliced into about 3 mm thick coronal sections, and one section was placed in 0.2% (v/v) Triton X-100 in phosphate buffered saline (PBS) at RT. After 5 d, the section was transferred into about 3 mL PBS and washed twice for 10 min each time. The section was then transferred to 1.0 mL PBS, and 30 µL NeuroTrace® 515/535 Yellow Fluorescent Nissl Stain (Molecular Probes, Eugene, Oreg.) and 1 µL TO-PRO®-3 (Molecular Probes, Eugene, Oreg.) was added. The specimen was then incubated in this solution at RT for about 48 hr on an orbital shaker. Following incubation, the section was transferred to 2.0 mL PBS for about 1 hr. The section was then transferred into fresh 2.0 mL PBS and stored for 5 d. After storage, the section was removed from PBS and the extra solution was removed with a low-lint wipe. The dried section was transferred into a solution of 56.25% (v/v) TCE 1.25% (v/v) TCA, 12.5% (v/v) glycerol, 30% (v/v) methanol and then placed into a shaking incubator at 37 C. After about 48 hr, the section was transferred to 100% glycerol and stored for 2 d until imaged. Images were collected on a Leica SPIT confocal microscope equipped with a HC PL APO 10x/0.40 objective and argon-krypton laser for excitation at 488 nm, 534 nm, 594 nm, and 633 nm.

Figure 22:
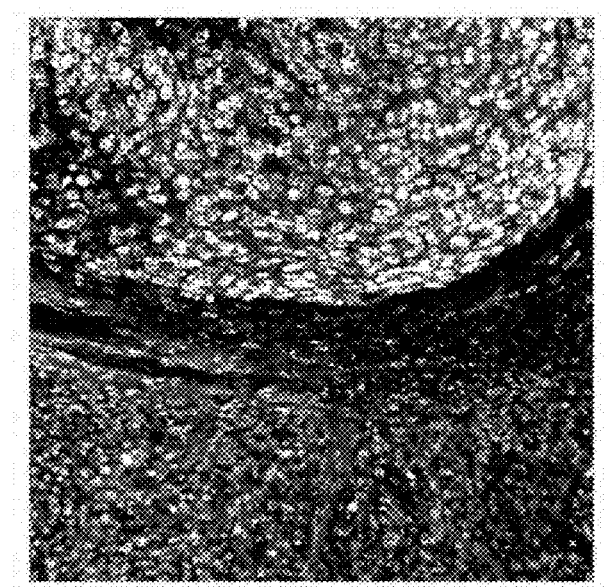
FIG. 22 is a representation of a micrograph of a mouse brain slice labelled with NeuroTrace® 515/535 Yellow Fluorescent Nissl Stain.

The image is shown in FIG. 22

Example 7

Human Specimens

Human placental cotyledon tissue, fixed with 10% neutral buffered formalin and stored for over one year in fixative solution, was transferred to PBS containing 0.01% (w/v) sodium azide for processing into small pieces. A tissue piece was washed 3 times in PBS and twice in 0.2% (v/v) Triton X-100 in PBS (PBST) for about 15 min each at RT. The tissue was then transferred to PBST containing 20% (v/v) dimethyl sulfoxide (DMSO) and 0.3 M glycine, and incubated for about 30 min at 37° C. The tissue was then blocked with PBS containing 0.2% Tween-20, 10% (v/v) DMSO and 6% (v/v) donkey serum for about 30 min at 37° C. The tissue was then washed 3 times in PBS containing 0.2% Tween-20 and 10 mg/ml heparin (PTwH) for about 15 min at 37° C. After washing, the tissue was then incubated for about 1 hr at 37° C. in a solution of 2.5 µL Anti-Ki67 antibody (ab15580) (Abcam, Cambridge, Mass.) in 500 µL PBS with 0.2% Tween-20, 5% (v/v) DMSO with 3% (v/v) donkey serum. After primary antibody treatment, the tissue was then washed 10 times at RT with PTwH for 5 min each. The tissue was then incubated for about 1 hr at 37° C. in a solution of 1 µL Goat Anti-Rabbit IgG H&L Alexa Fluor® 488 (ab150081) (Abcam, Cambridge, Mass.) mixed with 1000 µL 3% (v/v) donkey serum in PTwH. After secondary antibody treatment, the tissue was then washed 10 times at RT with PTwH for about 5 min each. Afterwards, the tissue was washed 3 times in PBST for 15 min at 37° C. The tissue was then incubated for about 30 min with a 1:1000 dilution of TO-PRO®-3 (Molecular Probes, Eugene, Oreg.) in PBST at 37° C. The tissue was then washed 3 times with 50% (v/v) absolute ethanol in PBS for about 15 min each at 37° C. The tissue was then washed 3 times with 70% (v/v) absolute ethanol in PBS for about 15 min each at 37° C. The tissue was then washed 3 times with absolute ethanol for about 15 min each at 37° C. Any remaining ethanol on the surface was dried with a low-lint wipe, and the tissue was transferred into a solution comprised of 33% (v/v) TCE, 33% (v/v) benzyl alcohol, and 33% (v/v) glycerol for 1 hr until clear. The tissue was stored in this solution until ready to image. Images were collected on a Leica SPII confocal microscope equipped with a HC PL APO 10x/0.40 objective and argon-krypton laser for excitation at 488 nm, 534 nm, 594 nm, and 633 nm.

Figure 23:
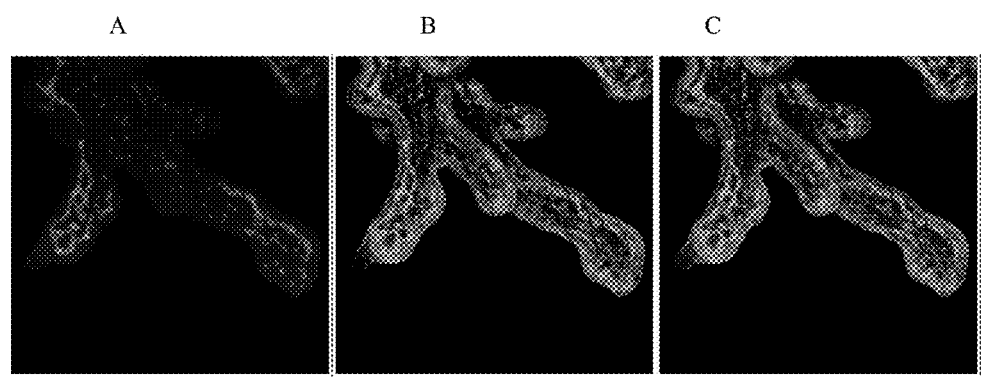
FIGS. 23A-23C are representations of micrographs of (a) human placental tissue labelled with TO-PRO-3; (b) placental tissue labelled with anti-Ki67 antibody and detected with AlexaFluor488 secondary antibody; and (c) human placental tissue labelled with both.

The results are shown in FIGS. 23A-C.

EQUIVALENTS

Those skilled in the art will recognize, or be able to ascertain, using no more than routine experimentation, numerous equivalents to the specific composition and procedures described herein. Such equivalents are considered to be within the scope of this disclosure, and are covered by the following claims.

The invention claimed is:
1. A clearing agent and mounting solution, comprising:
   5% to 97% (v/v) trichloroethanol or derivative thereof;
   16.5% to 36% (v/v) benzyl alcohol; and
   12.5% to 50% glycerol, polyethylene glycol (PEG), propylene glycol (PG), ethylene glycol (EG), and/or derivatives thereof; and optionally water.
2. The clearing agent and mounting solution of claim 1, comprising:
   36% (v/v) of trichloroethanol or derivative thereof;
   36% (v/v) benzyl alcohol; and
   27% (v/v) glycerol.
3. The clearing agent and mounting solution of claim 1, comprising:
   33% (v/v) of trichloroethanol or derivative thereof;
   33% (v/v) benzyl alcohol; and
   33% (v/v) glycerol.
4. The clearing agent and mounting solution of claim 1, comprising:
   33% (v/v) trichloroethanol or derivative thereof;
   33% (v/v) benzyl alcohol; and
   17% (v/v) glycerol; and further comprising:
   17% (v/v) benzyl benzoate.
5. The clearing agent and mounting solution of claim 1, comprising:
   29% (v/v) trichloroethanol or derivative thereof;
   29% (v/v) benzyl alcohol; and
   17% (v/v) glycerol; and further comprising:
   13% (v/v) benzyl benzoate; and
   13% (v/v) benzyl ether.
6. The clearing agent and mounting solution of claim 1, comprising:
   42% (v/v) trichloroethanol or derivative thereof;
   16.5% (v/v) benzyl alcohol; and
   16.5% (v/v) glycerol; and further comprising:
   25% (v/v) benzyl ether.
7. The clearing agent and mounting solution of claim 1, comprising:
   36% (v/v) of trichloroethanol or derivative thereof;
   36% (v/v) benzyl alcohol; and
   27% (v/v) PEG, PG, EG, and/or derivatives thereof.
8. The clearing agent and mounting solution of claim 1, comprising:
   33% (v/v) of trichloroethanol or derivative thereof;
   33% (v/v) benzyl alcohol; and
   33% (v/v) PEG, PG, EG, and/or derivatives thereof.
9. The clearing agent and mounting solution of claim 1, comprising:
   33% (v/v) of trichloroethanol or derivative thereof;
   33% (v/v) benzyl alcohol; and

17% (v/v) PEG, PG, EG, and/or derivatives thereof; and further comprising:
17% (v/v) benzyl benzoate.

10. The clearing agent and mounting solution of claim 1, comprising:
29% (v/v) of trichloroethanol or derivative thereof;
29% (v/v) benzyl alcohol; and
17% (v/v) PEG, PG, EG, and/or derivatives thereof; and further comprising:
13% (v/v) benzyl benzoate; and
13% (v/v) benzyl ether.

11. The clearing agent and mounting solution of claim 1, comprising:
42% (v/v) trichloroethanol or derivative thereof;
16.5% (v/v) benzyl alcohol; and
16.5% (v/v) PEG, PG, EG, and/or derivatives thereof; and further comprising:
25% (v/v) benzyl ether.

12. The clearing agent and mounting solution of claim 1, wherein the trichloroethanol derivative comprises mono- or poly-halogenated branched or unbranched alcohols, diols, glycols, aldehydes, aldehyde-hydrates, hemi-acetals, acetals, ketals, aminals, and hemi-aminals of at least 2 carbon units, wherein branches are defined as any mono- or poly-halogenated aliphatic or aromatic side chains containing hydroxyl, amino, ether, carboxyl, carboxyamido, carbonate, carbamyl, carbonyl-chloride, polyethylene glycol, or aminoethanol groups, and a polymer thereof.

13. The clearing agent and mounting solution of claim 1, further comprising C1-C6 alcohol.

14. The clearing agent and mounting solution of claim 1, further comprising a solidification aid comprising polyethylene glycol, polyamide resin, polyvinylpyrrolidone, polyvinyl alcohol, or mixtures thereof.

15. A clearing agent and mounting solution, comprising:
5% to 90% (v/v) trichloroethanol or derivative thereof; and
5% to 90% (v/v) benzyl alcohol.

* * * * *